US007205392B2

(12) United States Patent
Olsson et al.

(10) Patent No.: US 7,205,392 B2
(45) Date of Patent: Apr. 17, 2007

(54) HISTIDINE-RICH GLYCOPROTEIN

(75) Inventors: Anna-Karin Olsson, Uppsala (SE); Helena Larsson, Stockholm (SE); Lena Claesson-Welsh, Uppsala (SE)

(73) Assignee: Innoventus Project AB, Uppsala (SE)

( * ) Notice: Subject to any disclaimer, the term of this patent is extended or adjusted under 35 U.S.C. 154(b) by 652 days.

(21) Appl. No.: 10/067,093

(22) Filed: Feb. 4, 2002

(65) Prior Publication Data

US 2002/0165131 A1 Nov. 7, 2002

Related U.S. Application Data

(60) Provisional application No. 60/266,505, filed on Feb. 5, 2001.

(51) Int. Cl.
C07K 5/00 (2006.01)
(52) U.S. Cl. .................. 530/395; 530/350; 530/300
(58) Field of Classification Search ................ 530/300, 530/350
See application file for complete search history.

(56) References Cited

U.S. PATENT DOCUMENTS

| 4,946,778 A | 8/1990 | Ladner et al. |
| 5,545,806 A | 8/1996 | Lonberg et al. |
| 5,569,825 A | 10/1996 | Lonberg et al. |
| 5,854,205 A | 12/1998 | O'Reilly et al. |

FOREIGN PATENT DOCUMENTS

| WO | WO 91/06356 | 5/1991 |
| WO | WO 99/05263 | 2/1999 |
| WO | WO 00/26353 | 5/2000 |
| WO | WO 01/25410 | 4/2001 |
| WO | WO 01/62968 | 8/2001 |
| WO | WO 02/14369 | 2/2002 |
| WO | WO 02/064621 | 8/2002 |
| WO | WO 02/069885 | 9/2002 |

OTHER PUBLICATIONS

Saez et al., (Biochemistry, Feb. 28, 1995, vol. 34, issue 8, pp. 2496-2503).*
Kersemans et al., J Nucl Med. Mar. 2005;46(3):532-9, abstract only with this Office action.*
definition of "couple" as verb usage in Merriam-Webster Online dictionary downloaded on Aug. 8, 2005 from the internet site of M-W.com.*
Zamorano et al., (abstract only with this Office action) Stereotact Funct Neurosurg. 2003;81(1-4):10-7.*
definition of "couple" as verb usage in Merriam-Webster Online dictionary downloaded on Aug. 8, 2005 from the internet site of M-W.com, has been mailed already w/ the office action mailed on Aug. 10, 2005.*
Borza and Morgan, "Acceleration of Plasminogen Activation by Tissue Plasminogen Activator on Surface-bound Histidine-proline-rich Glycoprotein," *J. Biol. Chem.*, 1997, 272(8):5718-5726.

Borza and Morgan, "Histidine-Proline-rich Glycoprotein as a Plasma pH Sensor," *J. Biol. Chem.*, 1998, 273(10):5493-5499.
Brown et al., "Histidine-Rich Glycoprotein and Platelet Factor 4 Mask Heparan Sulfate Proteoglycans Recognized by Acidic and Basic Fibroblast Growth Factor," *Biochemistry*, 1994, 33:13918.
Hennis et al., "Evidence for the Absense of Intron H of the Histidine-Rich Glycoprotein (HRG) Gene: Genetic Mapping and in Situ Localization of HRG to Chromosome 3q28-q29," *Genomics*, 1994, 19:2195-2197.
Morgan, "Histidine-Rich Glycoprotein," *Encyclopedia of Molecular Medicine*, 2001, John Wiley & Sons, vol. 3, pp. 1644-1647.
Juarez et al., "Histidine-Proline-rich Glycoprotein Has Potent Antiangiogenic Activity Mediated through the Histidine-Proline-rich Domain," *Cancer Res.*, 2002, 62:5344-5350.
Zhang et al., "Two-chain high molecular weight kininogen induces endothelial cell apoptosis and inhibits angiogenesis: partial activity within domain 5," *FASEB J.*, 2000, 14:2589-2600.
GenBank Accession No. U32189.
GenBank Accession No. AF194028.
GenBank Accession No. AF194029.
GenBank Accession No. NM_000412.
Auerbach et al., "Assays for Angiogenesis: A Review," *Pharmac. Ther.*, 1991, 51:1-11.
Ausubel et al. (eds.), *Short Protocols in Molecular Biology*, 1992, Second Edition, Green Publishing Associates and John Wiley & Sons, New York, Chapter 11, pp. 11-1-11-54.
Beauchamp et al., "A New Procedure for the Synthesis of Polyethylene Glycol-Protein Adducts; Effects on Function, Receptor Recognition, and Clearance of Superoxide Dismutase, Lactoferin, and $\alpha_2$-Macroglobulin," *Analytical Biochemistry*, 1983, 131:25-33.
Borza et al., "Domain Structure and Conformation of Histidine—Proline Rich Glycoprotein," *Biochemistry*, 1996, 35:1925-1934.
Cole et al., "The EBV-Hybridoma Technique and its Application to Human Lung Cancer," *Monoclonal Antibodies and Cancer Therapy*, 1983, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
David and Reisfeld, "Protein Iodination with Solid State Lactoperoxidase," *Biochemistry*, 1974, 13(5):1014-1021.
Dieffenbach et al. (eds.), *PCR Primer—A Laboratory Manual*, 1995, Cold Spring Harbor Laboratory Press (Table of Contents only).
Dixelius et al., "Endostatin-induced tryosine kinase signaling through the Shb adaptor protein regulates endothelial cell apoptosis," *Blood*, 2000, 95(11):3403-3411.
Drasin and Sahud, "Blood-Type and Age Affect Human Plasma Levels of Histidine-Rich Glycoprotein in a Large Population," *Thromb. Res.*, 1996, 84(3):179-188.

(Continued)

*Primary Examiner*—Misook Yu
(74) *Attorney, Agent, or Firm*—Fish & Richardson P.C.

(57) ABSTRACT

The invention relates to histidine-rich glycoprotein (HRGP) polypeptides and the use of these polypeptides. The invention includes methods for the inhibition of angiogenesis by administering an HRGP polypeptide. The invention also includes pharmaceutical compositions and articles of manufacture comprising HRGP polypeptides, antibodies and receptors that bind to an HRGP polypeptide, HRGP-depleted plasma and polynucleotides, vectors and host cells that encode HRGP polypeptides.

7 Claims, 4 Drawing Sheets

OTHER PUBLICATIONS

Friedlander et al., "Definition of Two Angiogenic Pathways by Distinct $\alpha_v$ Integrins," *Science*, 1995, 270:1500-1502.

Gerwins et al., "Function of fibroblast growth factors and vascular endothelial growth factors and their receptors in angiogenesis," *Crit. Rev. Oncol./Hematol.*, 2000, 34:185-194.

Gilbert, *Developmental Biology*, 2000, Sixth Edition, Sinauer Associates, Inc., Sunderland, Massachusetts, Chapter 6, pp. 143-181.

Green et al., "Antigen-specific human monoclonal antibodies from mice engineered with human Ig heavy and light chain YACs," *Nature Genetics*, 1994, 7:13-21.

Heimburger et al., "Humanserumproteine mit hoher Affinität zu Carboxymethylcellulose, II[II]," *Hoppe Seyler's Z. Physiol. Chem.*, 1972, 353:1133-1140.

Hennis et al., "Identification and Genetic Analysis of a Common Molecular Variant of Histidine-rich Glycoprotein with a Difference of 2KD in Apparent Molecular Weight," *Thromb. Haemost.*, 1995, 74(6):1491-1496.

Hennis et al., "An Amino Acid Polymnorphism in Histidine-rich Glycoprotein (HRG) Explains 59% of the Variance in Plasma HRG Levels," *Thromb. Haemost.*, 1995, 74(6):1497-1500.

Hulett and Parish, "Mutine histidine-rich glycoprotein: Cloning, characterization and cellular origin," *Immunol. Cell Biol.*, 2000, 78:280-287.

Huse et al., "Generation of a Large Combinatorial Library of the Immunoglobulin Repertoire in Phage Lambda," *Science*, 1989, 246:1275-1281.

Joki et al., "Continuous release of endostatin from microencapsulated engineered cells for tumor therapy," *Nature Biotech.*, 2001, 19:35-39.

Kluszynski et al., "Zinc as a Cofactor for Heparin Neutralization by Histidine-rich Glycoprotein," *J. Biol. Chem.*, 1997, 272(21):13541-13547.

Köhler and Milstein, "Continuous cultures of fused cells secreting antibody of predefined specificty," *Nature*, 1975, 256:495-497.

Koide et al., "The heparin-binding site(s) of histidine-rich glycoprotein as suggested by sequence homology with antithrombin III," *FEBS Lett.*, 1986, 194(2):242-244.

Koide et al., "Amino Acid Sequence of Human Histidine-Rich Glycoprotein Derived from the Nucleotide Sequence of Its cDNA," *Biochemistry*, 1986, 25:2219-2225.

Kozbor and Roder, "The production of monoclonal antibodies from human lymphocytes," *Immunol. Today*, 1983, 4(3):72-79.

Kunkel, "Rapid and efficient site-specific mutagenesis without phenotypic selection," *Proc. Natl. Acad. Sci. USA*, 1985, 82:488-492.

Lijnen et al., "Heparin Binding Properties of Human Histidine-rich Glycoprotein," *J. Biol. Chem.*, 1983, 258(6):3803-3808.

Matthews et al., "Enhanced Chemiluminescent Method for the Detection of DNA Dot-Hybridization Assays," *Analytical Biochemistry*, 1985, 151:205-209.

Nygren, "Conjugation of Horseradish peroxidase to Fab Fragments with Different Homobifunctional and Heterobifunctional Cross-Linking Reagents," *J. Histochem. Cytochem.*, 1982, 30(5):407-412.

Pain and Surolia, "Preparation of Protein A-Peroxidase Monoconjugate Using a Heterobifunctional Reagent, and its use in Enzyme Immunoassays," *J. Immunol.Meth.*, 1981, 40:219-230.

Peterson et al., "Histidine-rich Glycoprotein Modulation of the Anticoagulant Activity of Heparin," *J. Biol. Chem.*, 1987, 262(16):7567-7574.

Read et al., "Local endostatin treatment of gliomas administered by microencapsulated producer cells," *Nature Biotech.*, 2001, 19:29-34.

Rylatt et al., "Autorosette Inhibition Factor: Isolation and Properties of the Human Plasma Protein," *Eur. J. Biochem.*, 1981, 119:641-646.

Sambrook et al. (eds.), *Molecular Cloning—A Laboratory Manual*, 1989, Second Edition, Cold Spring Harbor Laboratory Press, Cold Spring Harbor, New York, pp. 7.39-7.52.

Sambrook et al. (eds.), *Molecular Cloning—A Laboratory Manual*, 1989, Second Edition, Cold Spring Harbor Laboratory Press, Cold Spring Harbor, New York, pp. 16.1-17.44.

Shigekiyo et al., "Congenital Histidine-Rich Glycoprotein Deficiency," *Thromb. Haemost.*, 1993, 70(2):263-265.

Shigekiyo et al., "HRG Tokushima: Molecular and Cellular Characterization of Histidine-Rich Glycoprotein (HRG) Deficiency," *Blood*, 1998, 91:128-133.

Simantov et al., "Histidine-rich glycoprotein inhibits the antiangiogenic effect of thrombospondin-1," *J. Clin. Invest.*, 2001, 107:45-52.

Sørensen et al., "Determination of the disulphide bridge arrangement of bovine histidine-rich glycoprotein," *FEBS Lett.*, 1993, 328(3):285-290.

"Vascular Endothelial Growth Factor," *Mini-Reviews & Technical Information*, www.rndsystems.com, pp. 16-17.

Wennström et al., "The Platelet-derived Growth Factor β-Receptor Kinase Insert Confers Specific Signaling Properties to a Chimeric Fibroblast Growth Factor Receptor," *J. Biol. Chem.*, 1992, 267(19):13749-13756.

Workman et al., "UKCCCR guidelines for the welfase of animals in experimental neoplasia," *Lab. Animals*, 1988, 22:195-201.

Zehnder and Leung, "Histidine-rich glycoprotein: Is there a role in hemostasis or immune function?" *J. Lab. Clin. Med.*, 1995, 125:682-683.

Zola, *Monoclonal Antibodies: A Manual of Techniques*, 1987, CRC Press, Inc., Boca Raton, Florida, pp. 147-158.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.*, 1990, 111:2129-2138.

Lamb-Wharton et al., "Induction of T-Lymphocyte Adhesion by Histidine-Proline-Rich Glycoprotein and Concanavalin A," *Cellular Immunology*, 1993, 152:544-555.

Lazar et al., "Transforming Growth Factor α Mutation of Aspartic Acid 47 and Leucine 48 Results in Different Biological Activities," *Mol. Cell. Biol.*, 1988, 8(3):1247-1252.

Lederman et al., "A single amino acid substitution in a common African allele of the CD4 molecule ablates binding of the monoclonal antibody, OKT4," *Mol. Immunol.*, 1991, 28:1171-1181.

Li et al., "beta-Endorphin omission analogs: dissociation of immunoreactivity from other biological activities," *Proc. Natl. Acad. Sci. USA*, 1980, 77:3211-3214.

Olsen et al., "Histidine-rich glycoprotein binding to T-cell lines and its effects on T-cell substratum adhesion is strongly potentiated by zinc," *Immunology*, 1996, 88:198-206.

Schwartz et al., "A superactive insulin: [B10-aspartic acid] insulin(human)," *Proc. Natl. Acad. Sci. USA*, 1987, 84(18):6408-6411.

* cited by examiner

A

B

HISTIDINE-RICH GLYCOPROTEIN

CROSS REFERENCE TO RELATED APPLICATION

This application claims priority under 35 USC §119(e) to U.S. Provisional Application No. 60/266,505, filed Feb. 5, 2001, which is incorporated herein by reference in its entirety.

BACKGROUND OF THE INVENTION

1. Field of the Invention

This invention relates to the inhibition of angiogenesis, and more particularly to the use of histidine-rich glycoprotein (HRGP) as an inhibitor of angiogenesis.

2. Description of the Related Art

HRGP is a heparin-binding plasma protein identified by Heimburger at al. See, Heimburger et al. (1972) *Physiol. Chem.* 353:1133–1140. The average concentration of HRGP in plasma is around 100 µg/ml. See, Drasin and Sahud (1996) *Thrombosis Research* 84:179–188. The amino acid sequences of mouse, rat, (Hulett and Parish (2000) *Immunology and Cell Biology* 78: 280–287), rabbit (Borza et al. (1996) *Biochemistry* 35:1925–1934) and human (Koide et al. (1986) *Biochemistry* 25:2220–2225) HRGP have been resolved. Structurally, the HRGP molecule can be divided into three main domains. The amino-terminal domain, encompassing about 250 amino acid residues, contains two cysteine protease inhibitor (cystatin)-like stretches, which allows the classification of HRGP as a member of a cystatin superfamily together with α2HS glycoprotein and kininogen. There are six putative sites for N-linked glycosylation in the amino terminal portion of HRGP. A central domain contains tandem repeats of the pentapeptide [H/P]-[H/P]PHG (SEQ ID NO:1). Both the central domain and the 105 amino acid C-terminal domain are di-sulfide bonded to the cystatin-like stretches in the amino-terminal domain (Borza et al., 1996). HRGP binds heparin/heparan sulfates (Lijnen et al. (1983) *J. Biol. Chem.* 258:3803–3808) in a pH-dependent interaction (Peterson et al. (1987) *J. Biol. Chem.* 262: 7567–7574). The isolated histidine-proline-rich middle domain mediates heparin binding (Borza et al., 1996), but the amino terminal domain has also been implicated in heparin binding. See, Koide et al. (1986) *FEBS Lett.* 194: 242–244. A congenital deficiency of HRGP has been mapped to a single-nucleotide mutation, which results in replacement of Gly 85to Glu in HRGP. This mutation leads to inefficient processing of the protein, the majority of which is retained intracellularly. As a consequence, the serum levels of HRGP are reduced to 25–30% of normal levels. See, Shigekiyo et al. (1993) *Thromb. Haemost.* 70:263–265 and Shigekiyo et al. (1998) *Blood* 91:128–133.

Angiogenesis, the process of generating new blood vessels leading to neovascularization, is essential during embryonic development, ovulation, cyclical development of the uterine endometrium, wound healing, tissue and organ growth, inflammation and wound healing. Unbalanced neovascularization is believed to contribute to the pathogenesis of certain disease states, such as arthritis, psoriasis, hemangiomas, diabetic retinopathy and retrolental fibroplasia, and to allow tumor growth and metastasis to occur. See, e.g., U.S. Pat. No. 5,854,205. Tumor cells must attract new vessels to expand locally and produce metastasis.

SUMMARY

The invention is based on the discovery that the administration of HRGP to a mammal results in the inhibition of angiogenesis.

In one aspect, the invention features a composition comprising a substantially pure HRGP polypeptide. Typically, the substantially pure HRGP polypeptide has anti-angiogenic activity. In some embodiments, the composition can also include another agent that has anti-angiogenic activity. Such an agent is termed an anti-angiogenic agent herein. In some embodiments, the composition can also include an agent that has anti-neoplastic activity. Such an agent is termed an anti-neoplastic agent herein.

In one aspect, the invention features a pharmaceutical composition including an HRGP polypeptide, and an anti-angiogenic agent or an anti-neoplastic agent. The composition can include a pharmaceutical carrier acceptable for administration to a mammal. The HRGP polypeptide can include, for example, intact HRGP, a modified HRGP polypeptide or a fragment of intact HRGP. This fragment of intact HRGP may include, but is not limited to, the amino terminal domain, the central domain or the C-terminal domain of intact HRGP, or a fragment including at least one tandem repeat of the pentapeptide [H/P]-[H/P]PHG (SEQ ID NO:1). The anti-angiogeneic agent may be, for example, angiostatin, thrombostatin, endostatin, interferon-I, interferon-inducible factor 10, platelet factor 4 or a COX-2 inhibitor.

The invention also features a fragment of intact HRGP polypeptide that inhibits angiogenesis and that is not the N-terminal, central or C-terminal domain of HRGP.

Also featured in the invention are articles of manufacture including packaging materials and an HRGP polypeptide within the packaging material, wherein the packaging material includes a label or package insert indicating that the HRGP polypeptide is to be administered to a mammal for the inhibition of angiogenesis.

In another aspect, the invention features a method for inhibiting angiogenesis in a mammal. The method includes administering an HRGP polypeptide to the mammal. The mammal may have an angiogenesis-dependent cancer or may suffer from an angiogenesis-related condition. Such an angiogenesis-related condition may include, but is not limited to, myocardial angiogenesis, diabetic retinopathy, diabetic neovascularization, inappropriate wound healing or an inflammatory disease.

In another aspect, the invention features a method for identifying an anti-angiogenic polypeptide. The method can comprise measuring the effect of an HRGP polypeptide upon FGF-2 induced migration of primary bovine adrenal cortex capillary endothelial cells, and identifying the HRGP polypeptide as an anti-angiogenic polypeptide when FGF-2 induced migration is significantly decreased in the presence of the HRGP polypeptide. Alternatively, the method can comprise measuring the effect of an HRGP polypeptide upon chick chorioallantoic membrane angiogenesis, and identifying the HRGP polypeptide as an anti-angiogenic polypeptide when the chick chorioallantoic membrane angiogenesis is significantly decreased in the presence of the HRGP polypeptide. In another alternative, the method can comprise measuring the effect of an HRGP polypeptide upon growth of an angiogenesis-dependent tumor in a mammal, and identifying the HRGP polypeptide as an anti-angiogenic polypeptide when tumor growth is significantly decreased in the presence of the HRGP polypeptide. The HRGP polypeptide can be an HRGP fragment. The angiogenesis-dependent tumor can be, e.g., a fibrosarcoma, a neuroblatsoma, or a teratoma. The tumor can be raised in, e.g., a mouse or a rat.

Another aspect of the invention features antibodies that bind to an HRGP polypeptide. These antibodies may bind to the C-terminal domain, the central domain or the N-terminal domain of an HRGP polypeptide. Also included in the invention are antibodies that neutralize the ability of an HRGP polypeptide to inhibit angiogenesis, are agonistic for angiogenesis or are antagonistic for angiogenesis.

In yet another aspect, the invention features a method for inhibiting angiogenesis in a mammal by administering an antibody that binds to an HRGP polypeptide.

Also featured in the invention is a method for increasing angiogenesis in a mammal by administering an anti-HRGP antibody that is agonistic for angiogenesis.

Yet another aspect of the invention features a method of birth control that includes administering an HRGP polypeptide to a female mammal.

Other aspects of the invention feature an HRGP polypeptide coupled to a detectable marker or coupled to a toxin and a method of imaging neovascularization in a mammal by administering an HRGP polypeptide coupled to a detectable marker to the mammal.

Another aspect of the invention features a receptor that binds to an HRGP polypeptide.

Also featured in the invention is plasma depleted of HRGP, including human HRGP-depleted plasma.

Polynucleotides that encode HRGP polypeptides, vectors including these polynucleotides and host cells including these vectors are also featured in the invention.

Unless otherwise defined, all technical and scientific terms used herein have the same meaning as commonly understood by one of ordinary skill in the art to which the invention belongs. Although methods and materials similar or equivalent to those described herein can be used in the practice and testing of the present invention, suitable methods and materials are described. All publications, patent applications, patents and other references mentioned herein are incorporated by reference in their entirety. In case of conflict, the present specification, including definitions, will control. In addition, the materials, methods, and examples are illustrative only and are not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a graph depicting the inhibition of tumor growth with the administration of HRGP.

DETAILED DESCRIPTION

Figure 1:
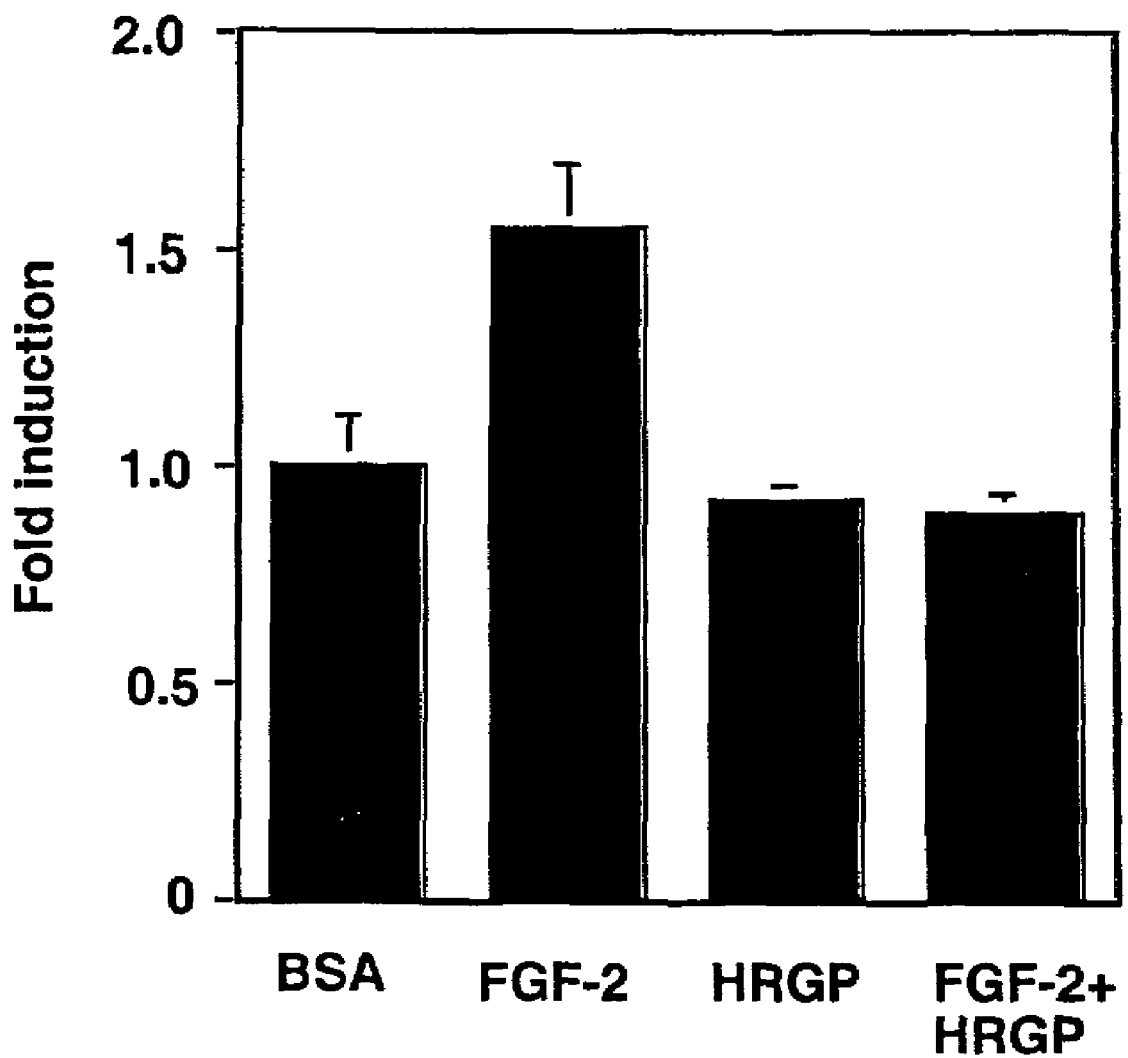
FIG. 1 shows the effects of HRGP on FGF-2 induced endothelial cell migration. Primary bovine capillary endothelial cells (BCE) were analyzed for their ability to migrate in a mini-Boyden chamber toward FGF-2, in the presence or absence of HRGP. Mean values±SEM of three different experiments are shown.

It has been discovered that purified human plasma HRGP inhibits chorioallantoic membrane (CAM) angiogenesis, endothelial cell migration and tumor growth. Treatment of the CAM with growth factors such as fibroblast growth factor 2 (FGF-2) or vascular endothelial cell growth factor A (VEGF-A) stimulates angiogenesis in the CAM. Surprisingly, the application of a ten-fold molar excess of HRGP, along with FGF-2 or VEGF-A, results in the suppression of angiogenesis. Primary bovine capillary endothelial (BCE) cells migrate toward FGF-2 with a 150% increase over basal migration in a mini-Boyden chamber. This increased migration was completely suppressed by co-incubation with HRGP. Finally, it was observed that injections of purified HRGP led to a drastic reduction in fibrosarcoma tumor growth in mice, with tumors being reduced by 75% in size. See Example 9 and FIG. 2. Based on these unexpected findings, HRGP polypeptides are a new and novel therapeutic agent for the treatment of diseases or processes that are mediated by, or involve, angiogenesis. HRGP polypeptides will be particularly useful for treating or repressing the growth of angiogenesis-dependent cancers.

The HRGP polypeptides of the current invention may be purified from freshly collected human serum or produced by well-known recombinant methodologies. HRGP polypeptides may be coupled to a detectable marker for diagnostic applications or coupled to a toxin for therapeutic applications. Pharmaceutical compositions comprising HRGP polypeptides may be administered to subjects in whom it is desired to inhibit angiogenesis. According to the current invention, HRGP polypeptides may also be used in combination with other compositions and procedures for the treatment of diseases. For example, HRGP polypeptides can be administered as pharmaceutical compositions that include, in addition, other anti-angiogenic compounds, anti-neoplastic compounds and/or anti-inflammatory compounds.

The present invention includes antibodies having specific binding affinity for HRGP polypeptides that can be used in either diagnostic or therapeutic applications. Particularly useful are neutralizing antibodies, capable of inhibiting or eliminating the biological activity of HRGP polypeptides. The invention further encompasses a method for identifying receptors specific for HRGP and the HRGP receptor molecules identified and isolated thereof. Antagonists of HRGP polypeptides, such as anti-HRGP antibodies or isolated HRGP receptor polypeptides may be administered to a subject in whom it is desired to promote angiogenesis.

The present invention also includes kits, comprising packaging materials and an isolated HRGP polypeptide, wherein the packaging material comprises a label or package insert indicating that the HRGP polypeptide is to be administered to a mammal for the inhibition of angiogenesis.

Production of HRGP Polypeptides

The invention provides substantially pure HRGP polypeptides. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment. As used herein, a substantially pure HRGP polypeptide may be at least 60 percent pure and can be at least about 65, 70, 75, 80, 85, 90, 95, or 99 percent pure. Typically, a substantially pure polypeptide will yield a single major band on a non-reducing polyacrylamide gel.

The cDNA and amino acid sequences of HRGP from several different species are known. The complete cDNA and amino acid sequences are known for human (Koide et al. (1986) *FEBS Lett.* 194:242–244), rat and mouse HRGP (Hulett and Parish (2000) *Immunology and Cell Biology* 78:280–287). A partial cDNA sequence, lacking the coding region for the leader sequence, and the full-length deduced amino acid sequence are known for rabbit HRGP. See, Borza et al. (1996) *Biochemistry* 35:1925–1934. A partial amino acid sequence of bovine HRGP, derived by direct protein sequencing is also available. See, Sorenson et al. (1993) *FEBS Lett.* 328:285. Five amino acid polymorphisms in human HRGP have been identified by Hennis et al.: Ile162, Pro 186, His322, Arg430 and Asn475. See, Hennis et al. (1995) *Thromb. Haemost.* 74:1491 and Hennis et al. (1995) *Thromb. Haemost.* 74:1497. Shigekiyo et al. have identified an additional Glu85 polyphorphism. See, Shigekiyo et al. (1998) *Blood* 91:128.

It will be appreciated that the term "HRGP polypeptide" includes not only intact HRGP, but also polypeptides that include any 6 or more amino acid residues of any portion of an art known HRGP sequence, regardless of post-translational modification. The term "HRGP polypeptide" also includes lengthened proteins or peptides wherein one or more amino acids are added to either or both ends of HRGP, or to an internal region of HRGP. The term "HRGP polypeptide" also includes HRGP polypeptides labeled with detectable moieties or toxins, such as ricin.

The term HRGP polypeptide includes polypeptides that contain one of the three main domains of the HRGP molecule, and functional fragments thereof. The amino-terminal domain, encompassing about 250 amino acid residues, contains two cysteine protease inhibitor (cystatin)-like stretches. There are six putative sites for N-linked glycosylation in the amino terminal domain of HRGP. The central domain contains tandem repeats of the pentapeptide [H/P]-[H/P]PHG (SEQ ID NO:1) and the C-terminal domain contains 105 amino acids. Both the central domain and the C-terminal domain are di-sulfide bonded to the cystatin-like stretches in the amino-terminal domain (See Borza et al., 1996). The isolated histidine-proline-rich middle domain mediates pH-dependent heparin binding (Borza et al., 1996). The amino terminal domain has also been implicated in heparin binding.

The term HRGP polypeptide includes, for example, shortened polypeptides that contain any 6–25 amino acids (e.g. 6, 7, 8, 9, 10, 11, 12, 13, 14, 15, 16, 17, 18, 19, 20, 21, 22, 23, 24 or 25 amino acid residues) of one of the art known HRGP sequences. It will be appreciated that the term HRGP polypeptide also includes polypeptides that contain an amino acid sequence that is greater than 25 amino acid residues (e.g., 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or more amino acid residues) in length and identical to any portion of one the art known HRGP sequences. Additional examples include, without limitation, polypeptides that contain an amino acid sequence that is 75 or more amino acid residues (e.g., 75, 100, 125, 150, 175, 200, 225, 250, 275, 300, 320, 325, 350, 390, or more amino acid residues) in length and is identical to any portion of an HRGP amino acid sequence.

In some embodiments, HRGP polypeptides retain the anti-angiogenic activity of intact HRGP polypeptide. Such HRGP polypeptides maintain at least 5% (e.g., 10%, 20%, 30%, 40%, 50%, 60%, 70%, 80%, 90%, 95%, 99%, 100%, or even more) of the anti-angiogenic activity of the full-length, intact HRGP. Anti-angiogenic activity is assayed in the CAM or endothelial cell migration assays, described below.

Also included in the definition of "HRGP polypeptide" are "modified HRGP polypeptides." Such modified HRGP polypeptides may retain anti-angiogenic activity or may even show increased activity. Modified HRGP polypeptides include, but are not limited to, HRGP polypeptides with substitutions of naturally occurring amino acids at specific sites with other molecules, including but not limited to naturally and non-naturally occurring amino acids. Also included are HRGP polypeptides containing an amino acid sequence that contains a single insertion, a single deletion, a single substitution, multiple insertions, multiple deletions, multiple substitutions, or any combination thereof (for example, a single deletion together with multiple insertions). These various modifications can be produced using methods well known in the art, including polymerase chain reaction (PCR)-based techniques and in vitro site-directed mutagenesis, in order to introduce one or more amino acid changes or to truncate the protein coding sequence at predetermined amino acid residues. See, for example, Kunkel et al. (1985) *Proc. Natl. Acad. Sci. USA*, 82:488–492.

Also included in the definition of modified HRGP polypeptides are HRGP polypeptides linked to other compounds, such as polyethylene glycol (PEG) polymers. The derivatization of amino groups on the surface of polypeptides, such as HRGP polypeptides, with PEG-containing compounds can extend the circulation lifetime of such polypeptides and reduce their potential antigenic properties. See, Beauchamp et al. (1983) *Anal. Biochem* 131(1):25–33. The molecular weight of PEG employed is not particularly limited, usually from 300 to 30,000, preferably from 1,000 to 15,000. The method of PEG modification may be any of those known in the art. See, for example, Beauchamp et al. (1983) *Anal. Biochem.* 131(1):25–33.

Further, a modified HRGP polypeptide within the scope of the invention can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino terminus. HRGP polypeptides also can be produced as fusions with enzymes that aid in the detection of the polypeptide, such as alkaline phosphatase.

Any method can be used to obtain a substantially pure HRGP polypeptide. For example, intact HRGP can be purified from freshly collected human plasma by chromatography on phosphocellulose in the presence of proteinase inhibitors following the procedures. See Rylatt et al. (1981) *Eur. J. Biochem.* 119:641–646 or Kluszynski et al. (1997) *J. Biol. Chem.* 272:13541–13547. The resultant protein is 95% pure as estimated by SDS-polyacrylamide gel electrophoresis (PAGE). HRGP domains, including the N-terminal domain, the C-terminal domain and the central domain, can be isolated from HRGP subjected to limited plasmin proteolysis following the method outlined in Borza et al. et al. (1996) *Biochemistry* 35:1925–1934. Any material can be used as a source to obtain a substantially pure polypeptide. For example, tissue culture cells expressing a particular polypeptide of interest can be used to obtain substantially pure polypeptide. In addition to polypeptide purification techniques such as affinity chromatography and HPLC, polypeptide synthesis techniques can be used to produce an HRGP polypeptide.

HRGP polypeptides may also be produced by recombinant methods. The cDNA sequences of rabbit (Borza et al. (1996) *Biochemistry* 35:1925–1934), rat, mouse (Hulett and Parish (2000) *Immunology and Cell Biology* 78:280–287) and human (Koide et al. (1986) *FEBS Lett.* 194: 242–244) HRGP are art known. Methods for the expression of a protein product from a cDNA clone are well known. See, for example, Maniatis et al. (1989) *Molecular Cloning: A Laboratory Manual*, Cold Spring Harbor Laboratory, N.Y., pages 16.1–17.44. The HRGP polypeptide produced can be either an intact HRGP polypeptide or a fragment of HRGP. Suitable expression systems include, without limitation, microorganisms such as bacteria (for example, *E. coli* and *B. subtilis*) transformed with recombinant bacteriophage DNA, plasmid DNA, or cosmid DNA expression vectors; yeast (for example, *Saccharomyces* and *Pichia*) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing fusion protein nucleotide sequences; or mammalian cell systems (for example, HEK, COS, CHO, BHK, 293, VERO, HeLa, MDCK, WI38, and NIH 3T3 cells) transformed with expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector such as herpes viruses, retroviruses, vaccinia viruses, attenuated vaccinia viruses, canary pox viruses, adenoviruses, adeno-associated viruses, lentiviruses and herpes viruses, among others.

Assays for Anti-Angiogenesis Activity

Anti-angiogenic activity can be assayed in the CAM assay, essentially as described in Friedlander et al. and Dixelius et al. See Friedlander et al. (1995) *Science* 5241: 1500 and Dixelius et al. (2000) *Blood* 95:3403. Briefly, making a 1×1 cm window in the shell exposes an avascular zone of the CAM of a fertilized chick embryo. The sample to be tested is applied to this avascular zone, the window is sealed with tape and the chick embryo is incubated for three more days. At this point, the CAM is inspected with a light microscope to see whether endothelial cell growth has been inhibited by the sample, thereby indicating that the tested sample is anti-angiogenic. A statistically significant decrease in CAM score of 1.0 or more, relative to the score of stimulator alone, indicates that an HRGP polypeptide has anti-angiogenic activity.

Alternatively, the anti-angiogenic activity of an HRGP polypeptide can be determined by assaying the effect of the HRGP polypeptide on suppression of FGF-2 induced migration of bovine capillary endothelial cells in a modified Boyden chamber. See Auerbach et al. (1991) *Pharmacol. Ther.* 51:1–11. A statistically significant decrease of at least 50% in FGF-2-induced migration, compared to migration in the presence of FGF-2 alone, indicates that an HRGP polypeptide has anti-angiogenic activity.

Anti-angiogenic activity of an HRGP polypeptide can also be determined by measuring the effect of the polypeptide on growth of an angiogenesis-dependent tumor in a mammal, e.g. fibrosarcoma growth in animals. An HRGP polypeptide that, upon administration to tumor-bearing mice, achieves a statistically significant inhibition of tumor volume is considered to have anti-angiogenic activity. In some embodiments, an anti-angiogenic HRGP polypeptide can result in a 10% reduction in tumor volume compared to a control polypeptide that is known to have no effect on tumor growth. In other embodiments, an anti-angiogenic HRGP polypeptide can reduce tumor volume by 15% or more, 20% or more, 30% or more, 50% or more, 75% or more, or 90% or more, compared to a control polypeptide that has no effect on tumor growth.

It is understood that to assess the effect of an HRGP polypeptide, a difference is considered statistically significant at a p value of $\leq 0.05$ with an appropriate parametric or non-parametric statistic, e.g., Chi-square test, Student's t-test, Mann-Whitney test, or F-test.

Compositions Comprising HRGP

A composition of the invention comprises an HRGP polypeptide. In some embodiments, the composition includes an anti-angiogenic agent or an anti-neoplastic agent. In some embodiments, a composition also includes a pharmaceutically acceptable carrier.

Anti-angiogenic agents include, but are not limited to, interferon-inducible protein 10 and fragments and analogs of interferon-inducible protein 10, TGF-beta, thrombospondin, interleukin-1 (IL-1), gamma and alpha interferon (IFN), tissue inhibitor of metalloproteinase-1 (TIMP-1), platelet factor 4 (PF4), protamine, fumagillin, angiostatin and the like.

Anti-neoplastic agents contemplated for use in this invention are those agents that are known as chemotherapeutic agents toxic to tumor cells. Chemotherapeutic agents include alkylating agents, antimetabolites, natural products, hormones and antagonists, biological response modifiers (such as interferon and hematopoietic growth factors), differentiating agents such as butyrate derivatives, antibodies to tumor antigens and other miscellaneous agents. Specific examples include, but are not limited to taxol, cyclophosphamide, carboplatinum, cisplatinum, cisplatin, gancyclovir, camptothecin, paclitaxel, hydroxyurea, 5-azacytidine, 5-aza-2'-deoxycytidine, suramin, retinoids, and the like. Use of chemotherapeutic agents is particularly useful in situations in which the mammal to be treated has a large preexisting tumor mass which is well vascularized. The chemotherapeutic agent serves to reduce the tumor mass and the HRGP polypeptide prevents or inhibits neovascularization within or surrounding the tumor mass.

Combination therapy is not limited to the use of a HRGP polypeptide in conjunction with an anti-angiogenic agent or anti-neoplastic agent. Combination therapy can also involve the use of an HRGP polypeptide in combination with an anti-inflammatory agent such as prednisone, a COX-2 inhibitor, and the like. Suitable anti-inflammatory agents include ibuprofen and aspirin.

Pharmaceutical compositions comprising HRGP can be administered by intravenous infusion, or can be injected subcutaneously, intramuscularly, intraperitoneally, intrarectally, intravaginally, intranasally, intragastrically, intratracheally, intrapulmonarily, intratumorally, or intralesionally. The dosage required depends on the choice of the route of administration, the nature of the formulation, the nature of the patient's illness, the subject's size, weight, surface area, age, and sex, other drugs being administered, and the judgment of the attending physician. Wide variations in the needed dosage are to be expected in view of the variety of routes of administration. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Pharmaceuticaly acceptable carriers are biologically compatible vehicles suitable for administration to a mammalian subject such as, for example, a human patient, e.g., physiological saline. Such pharmaceutical compositions typically contain from about 0.1 to 90% by weight (such as 1 to 20% or 1 to 10%) of a therapeutic agent of the invention in a pharmaceutically acceptable carrier. Injectable formulations of the composition may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol and the like). For intravenous injections, water-soluble versions of the compounds may be administered by the drip method, whereby a pharmaceutical formulation containing HRGP and a physiological expedient is infused. Physiologically acceptable carriers may include, for example, 5% dextrose, 0.9% saline, Ringer's solution or other suitable carriers. Intramuscular preparations, e.g., a sterile formulation of a suitable soluble salt form of the compounds, can be dissolved and administered in a pharmaceutical excipient such as 0.9% saline or 5% glucose solution. A suitable insoluble form of the compound may be prepared and administered as a suspension in an aqueous base or a pharmaceutically acceptable oil base, such as an ester of a long chain fatty acid (e.g. ethyl oleate). A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens. Methods of making such formulations are well known and can be found in, for example, "Remington's Pharmaceutical Sciences."

A therapeutically effective amount is an amount capable of producing a medically desirable result in a treated mammal, e.g., a human patient. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration is from approximately 0.01 to 1,000 mg/kg of body weight. For example, a preferred dosage may include, but is not limited to 0.01, 0.05, 0.1, 0.5, 1.0, 5.0, 10, 25, 50, 100, 500, 750 or 1,000 mg/kg of body weight. It is expected that the preferred administration will be intravenous.

An anti-angiogenic HRGP polypeptide can be administered to a subject in whom it is desired to inhibit angiogenesis. Appropriate subjects include, without limitation, those with any of a variety of angiogenic-dependent cancers such as rhabdomyosarcoma, glioblastoma multiforme, leiomyosarcoma, prostate carcinoma, mammary carcinoma, lung carcinoma, melanoma, bladder carcinoma, pancreatic carcinoma and renal carcinoma. Angiogenic diseases amenable to treatment using HRGP polypeptide include but are not limited to diabetic retinopathy, diabetic neovascularization, retrolental fibroplasia, trachoma, neovascular glaucoma, psoriasis, angio-fibromas, immune and non-immune inflammation, capillary formation within atherosclerotic plaques, myocardial angiogenesis, hemangiomas, excessive wound repair, various inflammatory diseases and any other disease characterized by excessive and/or deregulated angiogenesis.

Articles of Manufacture

HRGP polypeptides can be packaged as an article of manufacture that contains one or more unit dosage forms. The article of manufacture typically comprises at least one container with a label. This container may, for example, comprise glass or plastic bottles or vials, metal or plastic foil and may also include unit dose blister packaging. The container holds a composition comprising an HRGP polypeptide. The package may be accompanied by a label or packaging insert indicating that the HRGP polypeptide is to be administered for the inhibition of angiogenesis and may also indicate directions for in vivo or ex vivo use. These directions may indicate that the HRGP polypeptide may be used alone or in combination with other agents. The package may also include additional agents, such as additional anti-angiogenic agents, anti-neoplastic agents or anti-inflammatory agents. The article of manufacture may also comprise a second container comprising a suitable diluent or buffer. It may further include other materials desirable from a commercial and user standpoint, including buffers, filters, needles, syringes, and package inserts with instructions for use.

Antibodies to HRGP

Antibodies having specific binding affinity for HRGP polypeptide can be produced through standard methods. As used herein, the terms "antibody" or "antibodies" include intact molecules as well as fragments thereof that are capable of binding to an epitopic determinant in the HRGP polypeptide. The term "epitope" refers to an antigenic determinant on an antigen to which the paratope of an antibody binds. Epitopic determinants usually consist of chemically active surface groupings of molecules such as amino acids or sugar side chains, and typically have specific three dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and F(ab)$_2$ fragments. Monoclonal antibodies are particularly useful.

In general, a polypeptide of interest is produced recombinantly, by chemical synthesis, or by purification of the native protein, and then used to immunize animals. Various host animals including, for example, rabbits, chickens, mice, guinea pigs, and rats, can be immunized by injection of the polypeptide of interest. Adjuvants can be used to increase the immunological response depending on the host species, and include Freund's adjuvant (complete and incomplete), mineral gels such as aluminum hydroxide, surface-active substances such as lysolecithin, pluronic polyols, polyanions, peptides, oil emulsions, keyhole limpet hemocyanin (KLH), and dinitrophenol. Polyclonal antibodies are heterogeneous populations of antibody molecules that are specific for a particular antigen, which are contained in the sera of the immunized animals. Monoclonal antibodies, which are homogeneous populations of antibodies to a particular epitope contained within an antigen, can be prepared using standard hybridoma technology. See Kohler et al. (1975) *Nature* 256:495. In particular, monoclonal antibodies can be obtained by any technique that provides for the production of antibody molecules by continuous cell lines in culture, such as the human B-cell hybridoma technique (See Kosbor et al. (1983) *Immunology Today* 4:72 and Cole et al. (1983) *Proc. Natl. Acad. Sci. USA* 80:2026) or the EBV-hybridoma technique (See Cole et al. (1983) "Monoclonal Antibodies and Cancer Therapy", Alan R. Liss, Inc., pp. 77–96). Such antibodies can be of any immunoglobulin class including IgG, IgM, IgE, IgA, IgD, and any subclass thereof. The hybridoma producing the monoclonal antibodies of the invention can be cultivated in vitro or in vivo.

A chimeric antibody is a molecule in which different portions are derived from different animal species, such as those having a variable region derived from a murine monoclonal antibody and a human immunoglobulin constant region. Chimeric antibodies can be produced through standard techniques.

Humanized forms of the murine antibodies may be made by substituting the complementarity determining regions of the mouse antibody into a human framework domain, by methods known in the art. Selected murine framework residues also may be substituted into the human recipient immunoglobulin. Monoclonal antibodies with a desired binding specificity can be commercially humanized (Scotgene, Scotland; Oxford Molecular, Palo Alto, Calif.). Fully human antibodies, such as those expressed in transgenic animals are also features of the invention. See, for example, Green et al. (1994) *Nature Genetics* 7:13–21, U.S. Pat. No. 5,545,806 and U.S. Pat. No. 5,569,825.

Antibody fragments that have specific binding affinity for HRGP polypeptide can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse et al. (1989) *Science*, 246:1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

Once produced, antibodies or fragments thereof are tested for recognition of HRGP polypeptide by standard immunoassay methods including, for example, ELISA techniques or RIA. See, *Short Protocols in Molecular Biology*, Chapter 11, Green Publishing Associates and John Wiley & Sons, Edited by Ausubel, F. M et al., 1992. Suitable antibodies preferably have equal binding affinities for recombinant and native proteins.

The HRGP antibodies of the current invention can be packaged in a diagnostic kit comprising at least one HRGP-specific antibody described herein, which may be conveniently used to detect HRGP in a sample for research or diagnostic purposes. Antibodies to HRGP may be employed in any known assay method, such as competitive binding assays, direct and indirect sandwich assays, and immuno-precipitation assays. See Zola, *Monoclonal Antibodies: A Manual of Techniques*, pp. 147–158 (CRC Press, Inc., 1987). Competitive binding assays rely on the ability of a labeled standard (which may be HRGP polypeptide or an immunologically reactive portion thereof) to compete with the test sample analyte (HRGP) for binding with a limited amount of antibody. The amount of HRGP in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte, which remain unbound.

The HRGP antibodies of the current invention can be neutralizing antibodies, capable of substantially inhibiting or eliminating a biological activity of HRGP, such as the anti-angiogeneic activity of HRGP as assayed in the CAM assay. The HRGP antibodies of the current invention can also be agonistic or antagonistic of angiogenesis.

HRGP Coupled to a Detectable Marker

For diagnostic applications, HRGP polypeptides may be labeled with a detectable moiety. This detectable moiety is capable of producing, either directly or indirectly, a detectable signal. For example, the detectable moiety may be a radioisotope, such as $H^3$, $C^{14}$, $P^{32}$, $S^{35}$, or $I^{125}$; a fluorescent or chemiluminescent compound, such as fluorescein isothiocyanate, rhodamine, or luciferin; or an enzyme, such as alkaline phosphatase, beta-galactosidase or horseradish peroxidase. Any method known in the art for conjugating a polypeptide to a detectable moiety may be employed. See, for example, Hunter et al. (1962) *Nature* 144:945; David et al. (1974) *Biochemistry* 13:1014; Pain et al. (1981) *J. Immunol. Meth.* 40:219; and Nygren (1982) *Histochem. and Cytochem.* 30:407.

HRGP polypeptides may also be coupled to a detectable moiety useful for in vivo imaging to image areas of neovascularization. The HRGP polypeptide may be labeled with a detectable moiety such as a radio-opaque agent or radioisotope and administered to a host, preferably into the bloodstream, and the presence and location of the labeled HRGP polypeptide is assayed. The HRGP polypeptide may be labeled with any moiety that is detectable in a host, whether by nuclear magnetic resonance, radiology, or other detection means known in the art. Radioisotope can be, for example, $^{186}$Re, $^{188}$Re, $^{64}$Cu, $^{67}$Cu, $^{212}$Bi, $^{123}$i, $^{131}$I, $^{211}$At, $^{177}$Lu, $^{47}$Sc, $^{105}$Rh, $^{109}$Pd, $^{153}$Sm, $^{199}$Au, $^{99m}$Tc, $^{111}$In, $^{124}$I, $^{18}$F, $^{11}$C, $^{198}$Au, $^{75}$Br, $^{76}$Br, $^{77}$Br, $^{13}$N, $^{34m}$Cl, $^{38}$Cl, $^{52m}$Mn, $^{55}$Co, $^{62}$Cu, $^{68}$Ga, $^{72}$As, $^{76}$As, $^{72}$Se, $^{73}$Se, or $^{75}$Se.

HRGP Coupled to a Toxin

HRGP coupled to a toxin may be used as a therapeutic agent to target the HRGP receptor. HRGP polypeptides may be coupled to any toxic polypeptide that mediates a cytotoxic effect within the cytoplasm of a cell by procedures well known in the art. Preferred toxic polypeptides include ribosome inactivating proteins, e.g., plant toxins such as an A chain toxin (e.g., ricin A chain), saporin, bryodin, gelonin, abrin, or pokeweed antiviral protein (PAP), fungal toxins such as α-sarcin, aspergillin, or restrictocin, bacterial toxins such as diphtheria toxin (DT) or Pseudomonas exotoxin A, or a ribonuclease such as placental ribonuclease or angiogenin. Other useful toxic polypeptides are the pro-apoptotic polypeptides, e.g., Bax, Bad, Bak, Bim, Bik, Bok, or Hrk. Furthermore, more than one functional fragment (e.g. 2, 3, 4, 6, 8, 10, 15, or 20) of one or more (e.g., 2, 3, 4, or 6) toxins can be coupled to HRGP. Where repeats are included, they can be immediately adjacent to each other, separated by one or more targeting fragments, or separated by a linker peptide as described above. The invention also includes functional fragments of any of these polypeptides coupled to an HRGP polypeptide.

Isolation of the HRGP Receptor

The invention further encompasses a method for identifying receptors specific for HRGP polypeptides and the receptor molecules identified and isolated thereof. Using techniques well known in the art, HRGP peptides may be employed to develop affinity columns for the isolation of the HRGP receptor from cell lysates. Isolation of the HRGP receptor is followed by amino acid sequencing. From this amino acid sequence information, polynucleotide probes can be developed for use in cloning polynucleotide sequences that encode the HRGP receptor.

Therapeutic Methods of Inhibiting Angiogenesis

An anti-angiogenic HRGP polypeptide can be administered to a subject in whom it is desired to inhibit angiogenesis. Appropriate subjects include, without limitation, those with any of a variety of angiogenic-dependent cancers, such as rhabdomyosarcoma, glioblastoma multiforme, leiomyosarcoma, prostate carcinoma, mammary carcinoma, lung carcinoma, melanoma, bladder carcinoma, pancreatic carcinoma and renal carcinoma. Angiogenic diseases amenable to treatment using HRGP polypeptide include but are not limited to diabetic retinopathy, diabetic neovascularization, retrolental fibroplasia, trachoma, neovascular glaucoma, psoriases, angio-fibromas, immune and non-immune inflammation, capillary formation within atherosclerotic plaques, myocardial angiogenesis, hemangiomas, excessive wound repair, various inflammatory diseases and any other disease characterized by excessive and/or deregulated angiogenesis.

Typically, an anti-angiogenic HRGP polypeptide is administered in a pharmaceutical composition. For therapeutic applications, HRGP polypeptide is administered to a mammal, for example, a human, in a pharmaceutically acceptable dosage form. HRGP polypeptide may be administered intravenously as a bolus or by continuous infusion over a period of time, by intramuscular, subcutaneous, intra-articular, intrasynovial, intrathecal, oral, topical, or inhalation routes. Long-term, continuous local delivery of an HRGP polypeptide can be achieved by the implantation of microencapsulated HRGP polypeptide-secreting cells. See, for example, Read et al. (2001) *Nat. Biotechnol.* 19(1): 29–34 and Joki et al. (2001) *Nat. Biotechnol.* 19(1):35–39.

For the prevention or treatment of disease, the appropriate dosage of HRGP polypeptide will depend on the type of disease to be treated, the severity and course of the disease, the course of previous therapy, the patient's clinical history and response to the HRGP polypeptide, and the discretion of the attending physician. The HRGP polypeptide is administered to the patient at one time or over a series of treatments. Depending on the type and severity of the disease, about 0.01 to about 1000 mg of HRGP polypeptide/kg of patient body weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded.

The efficacy of treatment may be assessed by various parameters including tumor size reduction, as determined by measurement of cutaneous masses, as determined by X-rays, scans and other means of tumor size evaluation; lack of tumor progression, as evaluated by the methods listed above; reduced keloid formation, as determined by measurement and evaluation of superficial lesions; improvement of retinal lesions associated with diabetic retinopathy, as determined by comparative analysis of photographs of the retinal fundus and other appropriate methods of evaluation; lack of progression of diabetic retinopathy as determined by the method listed above. Blood pharmacological levels of HRGP polypeptide may be determined by ELISA, capture assays, radioimmunoassays, receptor binding assays and the like.

Therapeutic Methods of Promoting Angiogenesis

Antagonists of an anti-angiogenic HRGP polypeptide can be administered to a subject in whom it is desired to promote angiogenesis. Appropriate subjects include, without limitation, those with any of a variety of diseases amenable to treatment using an HRGP antagonist, and include but are not limited to peripheral ischemic disease, peripheral circulatory deficiency in diabetes and infertility. For therapeutic applications, an HRGP antagonist, such as an anti-HRGP antibody or an HRGP receptor, is administered to a mammal, for example, a human, in a pharmaceutically acceptable dosage form. The HRGP antagonist may be administered intravenously as a bolus or by continuous infusion over a period of time, by intramuscular, subcutaneous, intra-articular, intrasynovial, intrathecal, oral, topical, or inhalation routes. The appropriate dosage of HRGP antagonist will depend on the type of disease to be treated, the severity and course of the disease, the course of previous therapy, the patient's clinical history and response to the HRGP antagonist, and the discretion of the attending physician. The HRGP antagonist may be administered to the patient at one time or over a series of treatments.

Methods of Birth Control

An anti-angiogenic HRGP polypeptide can be used as a birth control agent by reducing or preventing the uterine vascularization required for embryo implantation. In such a method of birth control, an amount of HRGP polypeptide sufficient to prevent embryo implantation is administered to a female mammal. In one aspect of the birth control method, an amount of HRGP polypeptide sufficient to block embryo implantation is administered before or after intercourse and fertilization have occurred, thus providing an effective method for birth control, possibly a "morning after" method. Administration methods may include, but are not limited to, pills, injections (intravenous, subcutaneous, intramuscular), suppositories, vaginal sponges, vaginal tampons, and intrauterine devices.

HRGP-Depeleted Plasma

HRGP-depleted plasma may be prepared using anti-HRGP antibodies in various art known immunopurification techniques. Such techniques include, but are not limited to, immunoprecipitation, immunoaffinity bead purification and immunoaffinity column chromatography. HRGP-depleted plasma may also be prepared by passing plasma over a Ni-column prepared with Ni-NTA agarose resin (Qiagen Inc., Chatsworth, USA), by methods well known in the art.

Polynucleotides Encoding HRGP Polypeptides

Another aspect of the present invention includes isolated polynucleotide sequences encoding an HRGP polypeptide. Such polynucleotides include, but are not limited to, mRNAs, cDNAs and genomic DNAs, as well as diagnostically or therapeutically useful fragments thereof. Also included are variants of such polynucleotides, which variants encode for a fragment, derivative or analog of an HRGP polypeptide.

Isolated nucleic acid molecules of the invention can be produced by standard techniques. As used herein, "isolated" refers to a sequence corresponding to part or all of a gene encoding an HRGP polypeptide, but free of sequences that normally flank one or both sides of the wild-type gene in a naturally occurring genome. The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acids within the scope of the invention can be obtained using any method including, without limitation, common molecular cloning and chemical nucleic acid synthesis techniques. For example, PCR techniques can be used to obtain an isolated nucleic acid containing a nucleic acid sequence sharing identity with art known sequences of HRGP. PCR refers to a procedure or technique in which target nucleic acids are amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in "PCR Primer: A Laboratory Manual," Ed. by Dieffenbach, C. and Dveksler, G., Cold Spring Harbor Laboratory Press, 1995. When using RNA as a source of template, reverse transcriptase can be used to synthesize complimentary DNA (cDNA) strands.

Isolated nucleic acids of the invention also can be chemically synthesized, either as a single nucleic acid molecule or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

Isolated nucleic acids of the invention also can be obtained by mutagenesis. For example, an isolated nucleic acid that shares identity with an art known HRGP sequence can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain an isolated polynucleotide within the scope of the invention. For example, a sequence having homology to a nucleic acid sequence encoding an art known HRGP polypeptide or an amino acid sequence having homology to an art known HRGP amino acid sequence can be used as a query to search GenBank®. Examples of nucleic acids encoding known HRGP polypeptides include the following GenBank® Accession Nos.: NM 000412 (human); AF194028 (mouse); AF 194029 (rat); and U32189 (rabbit).

Furthermore, nucleic acid hybridization techniques can be used to obtain an isolated nucleic acid within the scope of the invention. Briefly, a nucleic acid sequence encoding an HRGP polypeptide can be used as a probe to identify a similar nucleic acid by hybridization under conditions of moderate to high stringency. Moderately stringent hybridization conditions include hybridization at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1–15 ng/mL probe (about $5 \times 10^7$ cpm/µg), and wash steps at about 50° C. with a wash solution containing 2×SSC and 0.1% SDS. For high stringency, the same hybridization conditions can be used, but washes are performed at about 65° C. with a wash solution containing 0.2×SSC and 0.1% SDS.

Once a nucleic acid is identified, the nucleic acid then can be purified, sequenced, and analyzed to determine whether it is within the scope of the invention as described herein. Hybridization can be done by Southern or Northern analysis to identify a DNA or RNA sequences, respectively that hybridizes to a probe. The probe can be labeled with biotin, digoxygenin, an enzyme, or a radioisotope such as $^{32}P$ or $^{35}S$. The DNA or RNA to be analyzed can be electrophoretically separated on an agarose or polyacrylamide gel, transferred to nitrocellulose, nylon, or other suitable membrane, and hybridized with the probe using standard techniques well known in the art. See, for example, sections 7.39–7.52 of Sambrook et al., (1989) "Molecular Cloning," second edition, Cold Spring Harbor Laboratory, Plainview, N.Y.

The present invention also includes vectors comprising isolated polynucleotides encoding HRGP polypeptides and host cells comprising these vectors. The vectors of the present invention may include, for example, cloning vectors or expression vectors. Host cells may be genetically engineered (transduced or transformed or transfected) with the vectors of this invention. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The invention will be further described in the following examples, which do not limit the scope of the invention described in the claims.

EXAMPLE 1

Tissue Culture

A porcine aortic endothelial (PAE) cell line overexpressing FGF receptor-1 (FGFR-1) was cultured in Ham's F12 medium supplemented with 10% fetal bovine serum (FCS). See, Wennström et al. (1992) *J. Biol. Chem.* 267:13749. Primary bovine adrenal cortex capillary endothelial (BCE) cells were cultured on gelatin-coated tissue culture dishes in Dulbecco's modified medium complemented with 10% FCS and 1 ng/ml FGF-2 (Boehringer Mannheim). U-343 MG human glioma cells were cultured in Dulbecco's modified medium complimented with 10% FCS. Swiss 3T3 fibroblasts were cultured in DMEM supplemented with 10% FCS. Human embryonic kidney (HEK) 293-EBNA cells were cultured in DMEM/10% FCS.

EXAMPLE 2

Chorioallantoic Membrane (CAM) Assay

The conditions for the CAM assay followed were essentially as described in Friedlander et al. and Dixelius et al. See Friedlander et al. (1995) *Science* 5241:1500 and Dixelius et al. (2000) *Blood* 95:3403. Fertilized chick embryos were purchased locally and preincubated for ten days at 38° C. with 70% humidity. A small hole was drilled directly over the air sac at the end of the egg. An avascular zone was identified on the CAM, and a second hole was made in the eggshell above that area. The CAM was separated from the shell by applying vacuum to the first hole. Filter discs (Whatman Inc.) were saturated with 3 mg/ml cortisone acetate (Sigma) and soaked in buffer (30 µl for each filter) with or without FGF-2 (Boehringer Mannheim; 0.2 µg for each filter), VEGF-A (Peprotech; 0.2 µg for each filter) and purified HRGP (3 µg for each filter). The CAM was exposed after making a 1×1 cm window in the shell, and the sample was added to an avascular part of the membrane. The windows were sealed with tape, and the chick embryos were incubated for three more days. At this point, the membrane was cut around the filter, which was turned upside down and inspected in a light microscope (Nikon Eclipse TE 300, magnification 2.5 or 4).

EXAMPLE 3

Endothelial Cell Migration Assay

The migration assay was performed in a modified Boyden chamber (See, Auerbach et al. (1991) *Pharmacol. Ther.* 51:1–11) using micropore nitrocellulose filters (8 µg thick, 8 µm pore) coated with type-1 collagen solution at 100 µg/ml (Vitrogen 100, Collagen Corp). Primary BCE cells or human glioma cells (U-343 MG) were preincubated with HRGP (100 ng/ml) for 30 min, trypsinized and resuspended at a concentration of $4.0 \times 10^5$ cells/ml in Ham's F12 medium containing 0.1% fetal calf serum (FCS). The cell suspension was placed in the upper chamber, and medium containing 0.1% FCS in combination with 5 ng/ml FGF-2 or 5 ng/ml platelet-derived growth factor-BB (PDGF-BB; Peprotech Inc.) and 100 ng/ml HRGP, individually or in combination, was placed below the filter in the lower chamber. FCS at 10% was used as a positive control. After 4 h at 37° C. the medium was removed and cells sticking to the filter were fixed in pure methanol and stained with Giemsa stain. Cells on the lower side of the filter were counted in three separate microscopic fields, using image analysis software (Easy Image Analysis) from Bergström Instruments, Sweden. All samples were analyzed in at least six wells for each treatment.

EXAMPLE 4

Animal Studies

Animal work was carried out at the animal facility of the Biomedical Center, Uppsala University, was approved by the local board of animal experimentation and performed according to the UKCCCR guidelines for the welfare of animals in experimental neoplasia. See, Workman et al. (1988) *Lab. Anim.* 22:195–201. Female, 6 week old, C57BL6/J mice (Mollegard/Bomhultgard, Denmark) were acclimatized and caged in groups of five and were fed a diet of animal chow and drinking water ad lib. The mice were anesthetized with isoflurane (Forene; Abbott, Sweden) during all manipulations. T241 fibrosarcoma cells, $0.5 \times 10^6$ in 50 µl DMEM, were injected subcutaneously into the left flank of the mouse. Animals carrying palpable tumors were randomized and received treatment with 4 mg/kg/day of HRGP or vehicle (PBS) or as a control, thermolysin-cleaved antithrombin, given as daily subcutaneous injections in the right flank for eleven days. The tumors were measured with a caliper once a day, in a double-blind procedure, and volumes were calculated by the formula $\pi/6 \times \text{width}^2 \times \text{length}$. Statistical analysis was performed using ANOVA. After about 11 days of treatment mice were sacrificed with a lethal dose of pentobarbitone and perfused with 4% paraformaldehyde in Millonig's phosphate buffer pH 7.4. Tumors were then embedded in paraffin according to standard histological procedures and sectioned at 4 µm thickness.

EXAMPLE 5

Immunoprecipitation and Blotting

PAE/FGFR-1 cells described in Example 1 were serum-starved overnight, and stimulated or not with FGF-2 (100 ng/ml) or HRGP (1 µg/ml), individually or in combination, for 10 min at 37° C. The cells were lysed in Nonidet P40-containing buffer, samples were separated by SDS-PAGE and transferred to Hybond-C extra (Amersham Pharmacia Biotech). The membranes were immunoblotted with anti-phosphoErk1/2 antibodies (New England Biolabs Inc.) or anti-phosphop38 antibodies (New England Biolabs Inc.). Immunoreactive proteins were visualized by a chemiluminescence detection system. See, Matthews et al. (1985) *Anal. Biochem.* 151:205–209.

EXAMPLE 6

HRGP inhibits CAM Angiogenesis

The CAM of 10-day chick embryos was exposed by making a window in the shell. Treatment of the CAM with growth factors, such as FGF-2, stimulated angiogenesis in the CAM (Table 1). Application of FGF-2 or VEGF-A together with a ten-fold molar excess of HRGP on the CAM resulted in the suppression of angiogenesis.

TABLE 1

Inhibitory effect of HRGP on chick chorioallantoic membrane angiogenesis induced by FGF-2 or VEGF-A (0.2 µg/filter).

| Stimulator | Inhibitor | Angiogenesis score |
|---|---|---|
| Buffer | — | 1.2 |
| FGF-2 | — | 2.4 |
| FGF-2 | HRGP | 1.3 |
| VEGF | — | 2.8 |
| VEGF | HRGP | 1.6 |

The score, from 0 (low) to 3 (high) was based on the number of vessel branch points, according to the method of Friedlander et al, 1995 and Dixelius et al., 2000. Average values for 5–6 embryos were recorded. The variability was less than 15%. These results indicate that HRGP has anti-angiogenic activity as measured by a chorioallantoic membrane assay.

EXAMPLE 7

HRGP Inhibits Endothelial Cell Migration

Angiogenesis is a collective term for a number of changes that vascular endothelial cells undergo to form a new vessel, such as proliferation, migration and differentiation. See, Gerwins et al. (2000) *Crit. Rev. Oncol. Hematol.* 34:185–194. Using the assay described in Example 3, the effect of HRGP on endothelial cell migration was analyzed. Primary bovine capillary endothelial (BCE) cells migrated toward FGF-2 with a 150% increase over basal migration in a mini-Boyden chamber. This increased migration was completely suppressed by co-incubation of FGF-2 with HRGP at 100 ng/ml (FIG. 1). In contrast, migration of U-343 MG human glioma cells towards PDGF-BB was not inhibited by HRGP. The results indicate that HRGP has anti-angiogenic activity as measured by an endothelial cell migration assay.

EXAMPLE 8

Signal Transduction

The effects of HRGP on FGF-2-induced signal transduction in endothelial cells were tested in the assay described in Example 5. PAE/FGFR-1 cells were treated with 100 ng/ml FGF-2 or 50 ng/ml VEGF-A for 7 min in the presence or absence of 1 μg/ml HRGP. Total cell lysates were prepared, and analyzed by SDS-PAGE and immunoblotting. HRGP did not affect VEGF-A or FGF-2 induced activation of MAP kinases such as Erk1/2, or FGF-2-induced activation of p38, indicating that FGF-2-mediated FGFR-1 activation and signal transduction was not affected by HRGP. There was a slight increase in the basal level of Erk1/2 and p38 activities in the HRGP-treated cells.

EXAMPLE 9

Inhibition of Fibrosarcoma Tumor Growth in Mice

Figure 2A:
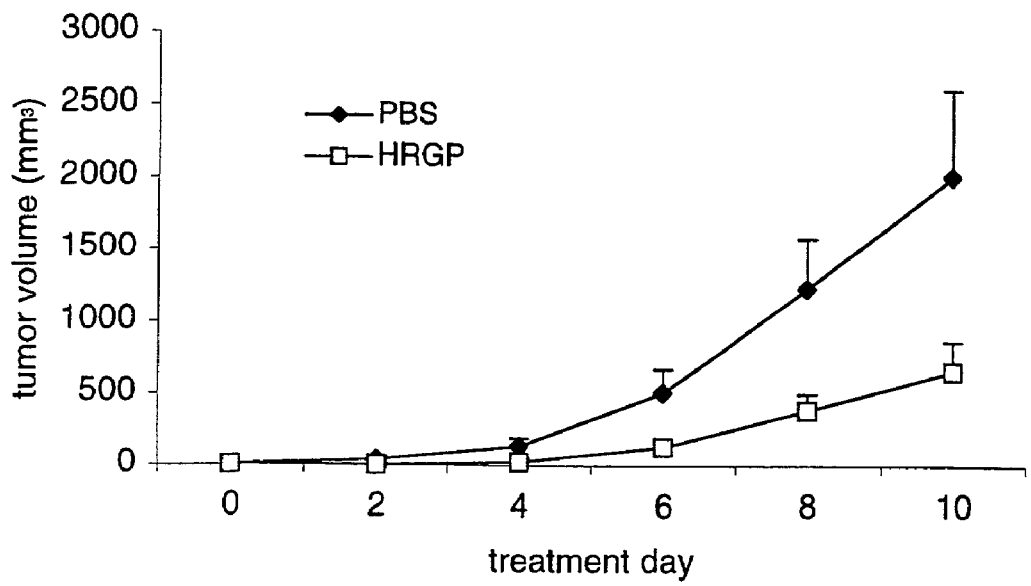
In FIG. 2A female-C57BL6/J mice were inoculated subcutaneously with 0.5× $10^6$ T241 cells in phosphate buffered saline (PBS). When tumors were palpable (treatment day 0), animals were randomly assigned to receive 11-day treatment with 4 mg/kg/day with HRGP (n=8) or PBS (n=10) by s.c. injection.
Figure 2B:
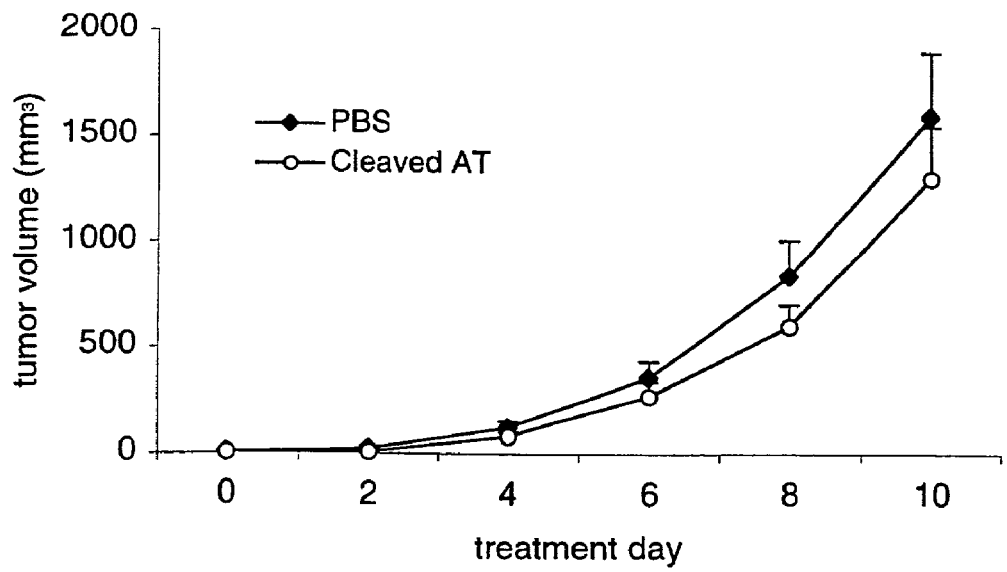
In FIG. 2B a parallel cohort of mice carrying palpable T241 tumors were injected with PBS (N=6) or with thermolysin-cleaved antithrombin (N=6). AT=thermolysin-cleaved antithrombin.

HRGP inhibited growth of fibrosarcoma in mice in the assay described in Example 4. HRGP purified from human plasma was used to treat C57/black mice, carrying palpable, subcutaneous T241 fibrosarcomas on their left flank. As a control, C57/black mice were treated with PBS. Treatments were given daily, as subcutaneous injections at a dose of 4 mg/kg in the right flank, until the size of the control tumor reached the upper level of 2.5 cm$^2$ (approximately 11 days). Injections with HRGP led to a drastic reduction in tumor growth (FIG. 2). At the time of sacrifice, the size of the tumors was reduced by about 75%. In parallel, tumor-bearing animals were treated with thermolysin cleaved anti-thrombin (FIG. 2B). There was no statistically significant difference in tumor size between PBS-treated animals and animals treated with thermolysin-cleaved anti-thrombin. These results indicate that the effect of pHRGP was not due to manipulations or injection of protein, in general, and that HRGP has anti-angiogenic activity as measured by a fibrosarcoma tumor growth assay.

EXAMPLE 10

Construction of HRGP Expression Vectors

Full-length cDNA encoding human histidine-rich glycoprotein (HRGP) was cloned into the EcoR1/Xhol sites in the pCEP-Pu2 expression vector. Hallgren et al, 2000). Amino acids 1–18 in the HRGP cDNA encode a signal peptide, which enables extra-cellular secretion of the protein. Therefore, the BM40 signal sequence in front of the cloning cassette in pCEP-Pu2 was removed by restriction cleavage with HindIII/Nhe1. The new vector was named pCEP-78544 and encodes HRGP without a His-tag (rHRGP).

Expression vectors for His-tagged full-length HRGP and C-terminally truncated variants were also constructed using the pCEP-Pu2 expression system. These vectors were made by PCR-amplification of either full-length or less than full-length portions of HRGP. A His-tag (six histidines) was added to the N-terminus of the HRGP coding region, to facilitate purification. An enterokinase cleavage site was introduced between the His-tag and the HRGP coding region, to allow removal of the His-tag. In these vectors, the HRGP signal sequence was excluded. Instead, the PCR-product was joined in frame with the BM40 signal sequence in pCEP-Pu2. Three such vectors were constructed, and named pCEP-Pu2/His 1, 3 and 4. The three vectors encode His-tagged, full-length HRGP (His 1) and two truncated HRGP polypeptides, (His 3–4). See FIG. 3.

EXAMPLE 11

Transfection of EBNA-293 Cells and Collection of Conditioned Media

Human embryonic kidney (HEK) 293-EBNA cells were used to produce recombinant HRGP polypeptides. These cells are stably transfected with the EBNA-1 gene, which is also expressed by the pCEP-Pu2 vector, to prevent chromosomal integration of transfected plasmid DNA. This manipulation allows for high plasmid copy number in the cytoplasm of the cell and increases the yield of recombinant protein. The HRGP expression vectors described in Example 10 were transfected into the 293-EBNA cell line using Lipofectamine (Invitrogen) according to the manufacturers protocol. About 48–72 hours after transfection, the cells were put under selective pressure with 2.5 μg/ml puromycin (Sigma), to select for uptake of the pCEP-Pu2 vector, and 0.25 mg/ml G418 (Calbiochem) to select for EBNA-1 expressing cells. Growing cells were expanded and conditioned media was collected every fifth day. To avoid contamination by bovine HRGP, FCS was exchanged to a defined serum-replacement media, TCM (ICN Biomedicals), during collection of conditioned media. Cells and debris were removed by centrifugation for 10 min at 1200 g.

EXAMPLE 12

Purification of HRGP from Plasma (pHRGP) and Recombinant HRGP (rHRGP)

pHRGP was purified from freshly collected human plasma by chromatography on phosphocellulose in the presence of proteinase inhibitors (Rylatt et al., 1981; Kluszynski et al., 1997). The same method was used to purify untagged HRGP (rHRGP) from conditioned medium

EXAMPLE 13

Purification of His-tagged HRGP

His-tagged HRGP polypeptides were purified from the His 1, 3 and 4 transfected cell lines described in Example 11 using Ni-NTA agarose. About 50 ml HRGP-conditioned media was incubated with 200 μl 50% Ni-NTA agarose slurry "end-over-end" at 4° C. over night. The agarose was spun down and washed 3–4 times with PBS pH 7.0/1 M NaCl/0.1% Tween-20. The agarose was packed in a column and washed again as above. Bound material was eluted in fractions using 100 mM imidazol/20 mM Tris pH 8.0/0.1 M NaCl. Protein containing fractions were pooled and dialyzed against PBS pH 7.0. The final protein concentration was estimated by comparison with a BSA standard on SDS-PAGE and by the BCA Protein Assay Kit (Pierce).

EXAMPLE 14

Tunel Assay

Terminal deoxynucleotidyl transferase-mediated dUTP nick-end labeling (TUNEL) assays were carried out as follows. BCE cells were seeded on gelatin-coated glass-slides in DMEM/10% NCS with 2 ng/ml FGF-2. After 48 hours, the medium was changed to starvation medium (DMEM/0.5% NCS) containing either 10 ng/ml FGF-2, 1 μg/ml rHRGP or the combination of the two. Forty four hours later, the cells were fixed in 4% paraformaldehyde and apoptotic cells stained using the In Situ Cell Detection Kit, Fluorescein (Roche Diagnostics). Briefly, the principle of the method is to label free 3'-OH ends, generated during the apoptotic process, with fluorescent dUTP in an enzymatic reaction. To be able to detect all cells, double staining with Hoechst 33342 was performed. The percentage TUNEL-positive cells was determined by analyzing approximately 1500 cells from each treatment.

EXAMPLE 15

Analysis of FGFR Activation

Analysis of FGF-receptor (FGFR) activation was performed using PAE/FGFR-1 cells, serum-starved overnight in F12/0.1% BSA and stimulated with FGF-2 (50 ng/ml) or rHRGP (1 μg/ml) or the combination, for 8 min at 37° C. The cells were lysed in Triton X-100-containing buffer and tyrosine phosphorylated proteins were immunoprecipitated using the 4G10 antibody (Upstate Biotechnology). The samples were separated by SDS-PAGE and transferred to Hybond-C extra (Amersham Pharmacia Biotech). Immunoblotting was performed with an anti-FGFR-1 antibody provided by Dr. P Maher, Scripps Research Institute, La Jolla, Calif., USA. Analysis of p38 phosphorylation was performed in PAE/FGFR-1 cells treated for 10 or 30 min at 37° C. with 50 ng/ml FGF-2, with or without preincubation with 1 μg/ml rHRGP for 30 min before addition of FGF-2. The cells were lysed in Triton X-100-containing buffer and total lysates were separated by SDS-PAGE and immunoblotted with anti-phosho-p38 and anti-p38 antibodies (New England Biolabs Inc.). Analysis of ERK1/2 phosphorylation was performed in BCE cells treated for 10 or 90 min at 37° C. with 50 ng/ml FGF-2, with or without preincubation with 1 μg/ml rHRGP for 30 min before addition of FGF-2. The cells were lysed in Triton X-100-containing buffer and total lysates were separated by SDS-PAGE and immunoblotted with anti-phospho-ERK antibody (New England Biolabs Inc.). Immunoreactive proteins were visualized by a chemiluminescence detection system (Matthews et al., 1985).

EXAMPLE 16

Production and Characterization of Recombinant HRGP

To further investigate the anti-angiogenic action of HRGP and to determine a minimal active region of the protein, recombinant HRGP was produced (rHRGP). Full-length HRGP was constructed with and without a His-tag and isolated as described in Examples 10–13. Two C-terminally truncated HRGP polypeptides with His-tags were produced and isolated as described in Examples 10–11 and 13.

Coomassie staining of isolated pHRGP polypeptide and isolated rHRGP polypeptide revealed that the recombinant protein displayed a slightly smaller apparent molecular weight, possibly due to different levels of glycosylation. Western blotting with an HRGP-specific antibody, revealed apart from the full-length protein, a number of smaller fragments in both the pHRGP and the rHRGP fraction. Isolated His 1, 3 and 4 HRGP polypeptides were also analyzed by Coomassie staining and anti-HRGP Western blot. The predicted molecular masses were as expected and all three recombinant proteins were recognized by an HRGP-specific antibody. The shortest truncated HRGP polypeptide, His 3, appeared to be more sensitive to proteolytic cleavage than the His 1 and 4 HRGP polypeptides.

Figure 3:
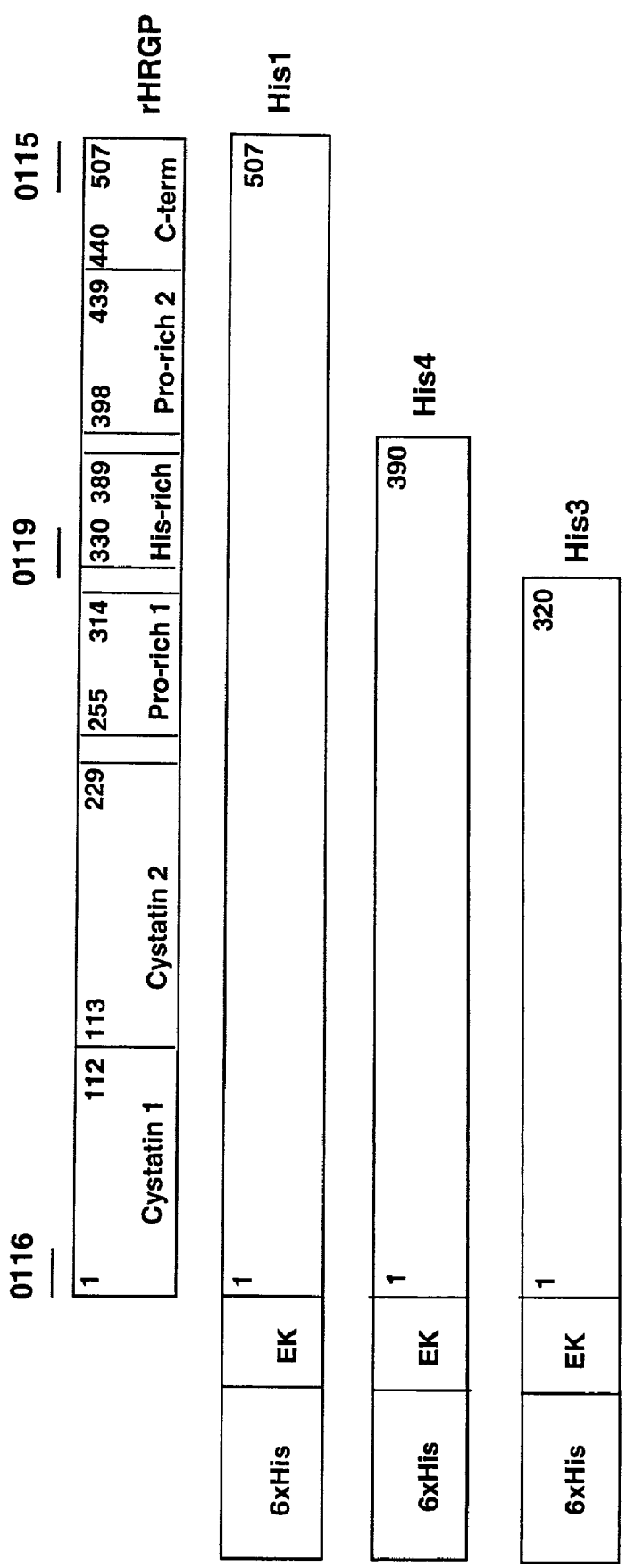
FIG. 3 shows major domains of HRGP including: an N-terminal cystatin-like part, a histidine/proline-rich middle domain and a C-terminal region. Also shown are a full-length HRGP with a His-tag (His 1) and two C-terminally truncated polypeptides (His 3–4). 6×His=His-tag, EK=enterokinase cleavage site. The numbers 390 and 320 indicate the C-terminal residue of the truncated polypeptides. The bars labeled 0115, 0116 and 0119 indicate the positions of the peptides against which rabbit antibodies were raised.

Domain-specific antibodies against HRGP were raised by immunizing rabbits with three different peptides, designated 0115, 0116 and 0119. The positions of these peptides in the HRGP protein are indicated in FIG. 3. Western blots of full-length HRGP were carried out, using the three anti-peptide antibodies. The results indicated that the full-length HRGP polypeptide was detected by all three antibodies. However, a specific pattern of reactivity was observed for each of the three antibodies against smaller HRGP-derived fragments.

EXAMPLE 17 rHRGP Inhibits Endothelial Cell Migration

Figure 4A:
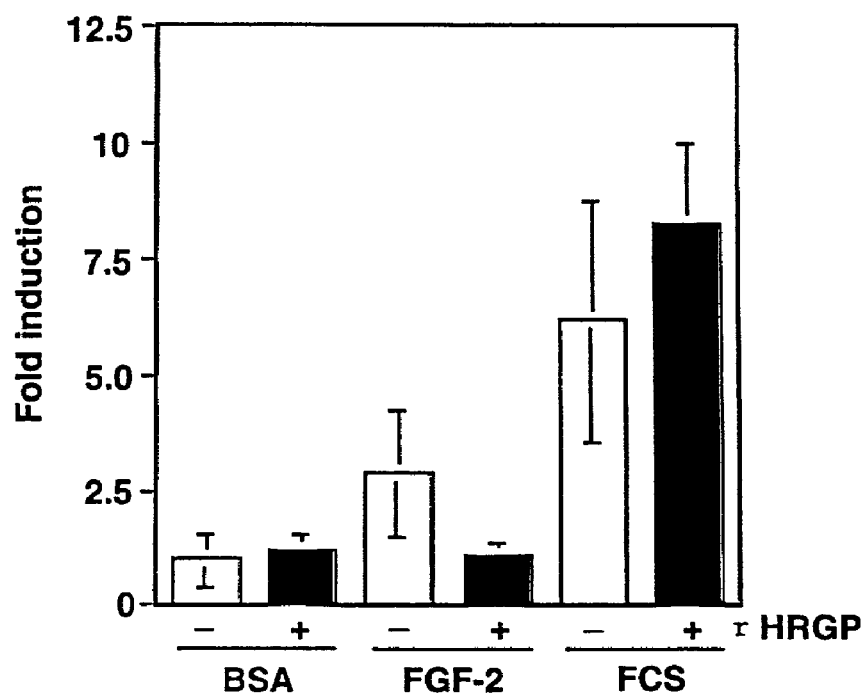
FIG. 4 shows the effect of rHRGP on FGF-2- and serum-induced migration. A. FGF-induced migration of BCE cells was inhibited by 100 ng/ml rHRGP. Serum (FCS)-induced migration was not inhibited by HRGP. B. Dose-response curve of rHRGP against FGF-induced migration of BCE cells. FGF-2 was used at 5 ng/ml.

The effect of rHRGP on endothelial cell migration was measured using the assay described in Example 3. The same inhibitory effect on FGF-induced migration seen with pHRGP was also observed when rHRGP was used (FIG. 4A). The inhibitory effect of rHRGP was statistically significant. Migration induced by fetal calf serum, however, was not inhibited by rHRGP. See FIG. 4A.

Figure 4B:
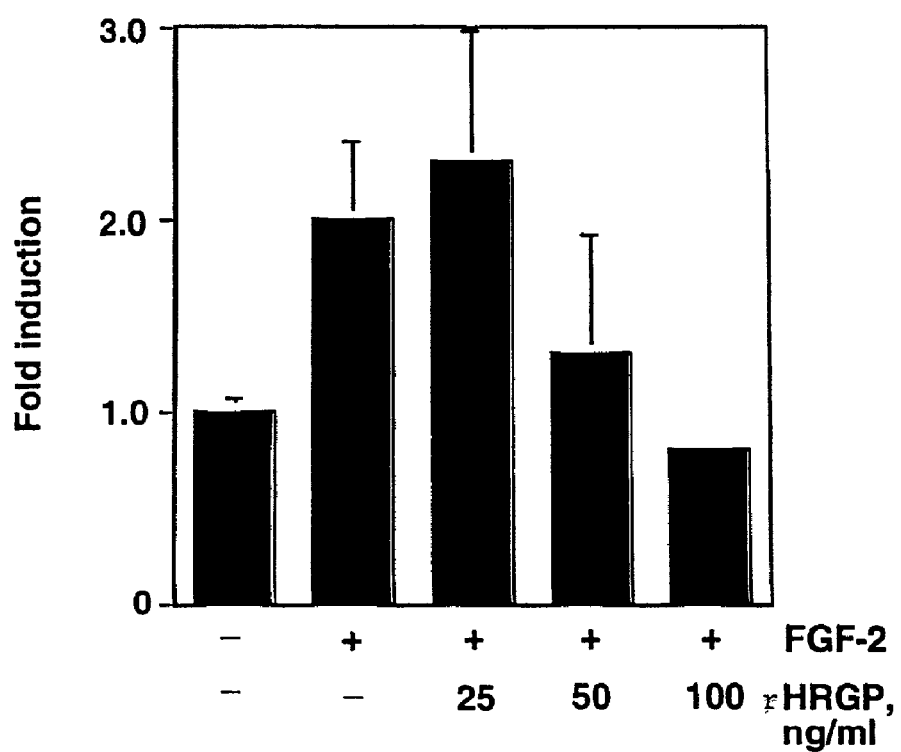

The assay was also carried out using varying amounts of rHRGP. As shown in FIG. 4B, 100 ng/ml rHRGP was needed to inhibit the migration to basal level. The presence of a His-tag did not affect the ability of His 1 HRGP to inhibit FGF-induced migration.

The effect of rHRGP against the growth factors VEGF-A and platelet derived growth factor BB (PDGF-BB) was also analyzed. VEGF-A and PDGF-BB also induce migration of BCE cells in culture. rHRGP completely prevented growth factor-induced migration by either VEGF-A or PDGF-BB. To exclude the possibility that any heparin-binding plasma protein of approximately the same size as HRGP could affect FGF-induced migration, we measured the effect of protein C inhibitor (PCI) polypeptide in the migration assay. The presence of PCI, in the absence of HRGP, had no effect on FGF-induced migration. The effect on FGF-induced endothelial cell migration of rHRGP alone was compared to that of endostatin (ES) alone. ES is a known anti-angiogenic agent. Both rHRGP and ES were used at 100 ng/ml, which corresponds to a molar ratio of 1:3 between HRGP and ES. Both rHRGP and ES inhibited FGF-induced migration to at least basal level, with ES being slightly more effective. To investigate the cell-specificity of the effects of rHRGP, we tested its ability to inhibit FGF-induced migration of Swiss 3T3 murine fibroblasts. When 3T3 cells replaced BCE cells in the assay, rHRGP had no effect on cell migration, indicating that the biological activity of rHGRP is specific for endothelial cells.

EXAMPLE 18

HRGP Inhibits FGF-induced Survival of Endothelial Cells

A TUNEL assay was carried out as described in Example 14. BCE cells seeded on gelatin-coated glass-slides were put in medium containing low serum (DMEM/0.5% NCS), and additions of FGF-2 and rHRGP were made either individually or in combination, at 10 ng/ml FGF-2 and 1 µg/ml rHRGP. The percentage TUNEL-positive cells in each treatment was determined.

FGF-2 induced a three-fold reduction in the percentage of apoptotic (TUNEL-positive) cells in starvation medium. The FGF-induced survival of endothelial cells was abolished when rHRGP was added together with FGF-2. rHRGP alone had no effect

EXAMPLE 19

Signal Transduction

We tested the effect of HRGP on FGF-2-induced signal transduction in endothelial cells. The effect on FGF-receptor-1(FGFR-1) activation was investigated by treating PAE/FGFR-1 cells with 50 ng/ml FGF-2 for 8 min, preincubated or not with 1 µg/ml rHRGP for 30 min. Total cell lysates were prepared and tyrosine phosphorylated proteins were immunoprecipitated. The samples were separated by SDS-PAGE and immunoblotted with anti-FGFR-1 antibody. The results showed that rHRGP did not affect FGF-2-induced activation of FGFR1.

The effect of rHRGP on p38 MAPK activation was analyzed in PAE/FGFR-1 cells. p38 MAPK has been associated with apoptosis in endothelial cells. The cells were treated for 10 or 30 min with 50 ng/ml FGF-2, with or without preincubation with 1 µg/ml rHRGP for 30 min before addition of FGF-2. Total lysates were separated by SDS-PAGE and immunoblotted with an anti-phosho-p38 antibody. FGF-2 induced increased phosphorylation of p38 at both 10 and 30 min of stimulation, but there was no effect of HRGP. Immunoblotting with an anti-p38 antibody revealed an equal amount of protein in each lane.

EXAMPLE 20

Tumor Growth in Mice

Tumor-bearing mice are prepared in a manner similar to that described in Example 4, using neuroblastoma cells instead of T241 fibrosarcoma cells and an appropriate site of introduction into the animals. Mice carrying detectable tumors are randomized and receive treatments with HRGP, vehicle (PBS) alone, or a negative control polypeptide that has no effect on tumor growth, such as thermolysin-cleaved AT or immunoglobulin G. HRGP, vehicle and control polypeptide are administered daily. Tumors are measured once a day, or at the time of administration, using a double-blind procedure. Tumor volumes are calculated by the formula $\pi/6 \times width^2 \times length$. Statistical analysis is performed using ANOVA or other appropriate statistical procedure. At the end of the experiment, mice are sacrificed using a lethal dose of pentobarbitone or other approved method of sacrifice, and are perfused with 4% paraformaldehyde in Millonig's phosphate buffer pH 7.4, or perfused with a buffer containing a labeled lectin that binds specifically to endothelial cells. Tumors are then embedded in paraffin or deep frozen according to standard histological procedures and sectioned at 4 µm thickness.

The experiment is repeated using an administration schedule of every other day, or an administration schedule of five days per week. The experiment is repeated using Lewis lung cells, teratoma cells, or other tumor cell models instead of neuroblastoma cells.

EXAMPLE 21

Effect of Truncated Forms of HRGP

Recombinant HRGP polypeptides His 3 and 4 are isolated as described in Example 13. The corresponding polypeptides without His tags are also isolated.

Each of the four polypeptides is tested in the CAM assay described in Example 2, the endothelial cell migration assay described in Example 3, the fibrosarcoma tumor assay described in Example 4, the signal transduction assay described in Example 8, and the TUNEL apoptosis assay described in Example 14.

EXAMPLE 22

Embryoid Body Angiogenesis

Mouse embryonic stem cells are induced to differentiate by withdrawal of LIF. Cells are aggregated in hanging drop cultures and, after four days, flushed into non-adherent petri dishes. The aggregates (embryoid bodies, EB) are treated in the petri dishes with one of the following: pHRGP, rHRGP, His 1, His 3, or His 4. As a control, EB are treated with ES as a positive control and PCI as a negative control. Formation of vascular plexa is analyzed qualitatively by immunohistochemistry using anti-CD31 antibodies on EB samples after 6, 8, 12 and 16 days in culture. For immunohistochemical staining, EB on glass slides are fixed in 4% paraformaldehyde, and permeabilized in methanol. Endogenous peroxidase activity is blocked in 3% $H2O2$ in methanol. Unspecific binding sites are blocked using the TNB blocking buffer kit (NEL 700; NEN Life Science Products), followed by incubation overnight with a primary rat-anti mouse CD31 antibody (Pharmingen) diluted 1:8000 in TNB. After washing, the samples are incubated with a secondary biotinylated goat-anti rat IgG (Vector), and subsequently with streptavidin-conjugated horseradish peroxidase and Biotinyl tyramide (from the NEL kit) to amplify the signal. For the enzyme reaction, the ABC reagent kit from Vector is used. EB in 3-D collagen gels are stained using a similar protocol, except for that incubation and washing time periods are extended and that washing is done with PBS containing Triton-X 100.

The embryoid bodies are also analyzed quantitatively to determine the size of the endothelial cell pool. This is done by collagenase treatment, followed by fluorescence-activated cell sorting (FACS) or isolation of endothelial cells through capturing on anti-CD31-coated magnetic beads.

The experiment is repeated by picking individual EB to glass slides, followed by treatment with an HRGP polypeptide as described above. The experiment is repeated by seeding EB in three-dimensional collagen gels, followed by treatment with an HRGP polypeptide as described above.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially pure histidine-rich glycoprotein polypeptide (HRGP) or HRGP fragment thereof having anti-angiogenic activity, wherein said HRGP or HRGP fragment thereof is coupled to a detectable marker, wherein said detectable marker is a fluorescent marker, a chemiluminescent marker, an enzymatic marker, or a magnetic resonance moiety.

2. The substantially pure histidine-rich glycoprotein polypeptide of claim 1, wherein said polypeptide is an HRGP fragment.

3. The substantially pure histidine-rich glycoprotein polypeptide of claim 2, wherein said HRGP fragment comprises at least one tandem repeat of the pentapeptide [H/P]-[H/P]PHG (SEQ ID NO:1).

4. The substantially pure HRGP fragment of claim 1, wherein said fragment is at least 40 amino acids in length.

5. The substantially pure histidine-rich glycoprotein polypeptide of claim 1, wherein said detectable marker is selected from the group consisting of fluorescein isothiocyanate, rhodamine, and luciferin.

6. The substantially pure histidine-rich glycoprotein polypeptide of claim 1, wherein said enzymatic marker is selected from the group consisting of alkaline phosphatase, beta-galactosidase, and horseradish peroxidase.

7. The substantially pure histidine-rich glycoprotein polypeptide of claim 1, wherein said detectable marker is a magnetic resonance moiety.

\* \* \* \* \*

UNITED STATES PATENT AND TRADEMARK OFFICE
CERTIFICATE OF CORRECTION

PATENT NO.        : 7,205,392 B2  
APPLICATION NO.   : 10/067093  
DATED             : April 17, 2007  
INVENTOR(S)       : Anna-Karin Olsson Page 1 of 1

It is certified that error appears in the above-identified patent and that said Letters Patent is hereby corrected as shown below:

Title Page, References Cited, Other Publications, second Hennis et al. reference, please delete "Polymnorphism" and insert --Polymorphism-- therefor;

Title Page, References Cited, Other Publications, Workman et al. reference, please delete "welfase" and insert --welfare-- therefor.

Signed and Sealed this

Eleventh Day of November, 2008

JON W. DUDAS  
*Director of the United States Patent and Trademark Office*

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1,2
<223> OTHER INFORMATION: Xaa=His or Pro

<400> SEQUENCE: 1

Xaa Xaa Pro His Glu
 1               5